United States Patent [19]

Bezzerides

[11] 4,383,389

[45] May 17, 1983

[54] POLLINATING MACHINE

[75] Inventor: Paul A. Bezzerides, Orosi, Calif.

[73] Assignee: Dave Vradenburg, Orosi, Calif.; a part interest

[21] Appl. No.: 310,606

[22] Filed: Oct. 13, 1981

[51] Int. Cl.³ .............................................. A01G 7/00
[52] U.S. Cl. .................................................... 47/1.41
[58] Field of Search .................................. 47/1.41, 1.5

[56] References Cited

U.S. PATENT DOCUMENTS

| | | |
|---|---|---|
| 1,866,219 | 7/1932 | Nielsen . |
| 2,171,160 | 8/1939 | Meiners . |
| 2,684,555 | 7/1954 | Kantack . |
| 2,685,149 | 8/1954 | Hvistendahl . |
| 2,775,065 | 12/1956 | Chepil et al. . |
| 3,728,817 | 4/1973 | Huey et al. . |

FOREIGN PATENT DOCUMENTS

| | | | |
|---|---|---|---|
| 473059 | 4/1951 | Canada | 47/1.41 |
| 407634 | 9/1966 | Switzerland | 47/1.41 |

*Primary Examiner*—Robert E. Bagwill
*Attorney, Agent, or Firm*—Huebner & Worrel

[57] ABSTRACT

A pollinating machine for use with plants growing in a row and having blossoms pollinated by compressing transversely of the row, the machine being mounted for movement along the row and having a pair of axially upright, cylindrical rollers spaced transversely of the row and provided individually with peripheral layers of resiliently yielding material, a pair of paddle wheels spaced transversely of the row ahead of the rollers, and mechanism rotationally driving the rollers and the wheels so that, as the machine moves along the row, the wheels gather the plants centrally of the row for compressing between the rollers.

8 Claims, 5 Drawing Figures

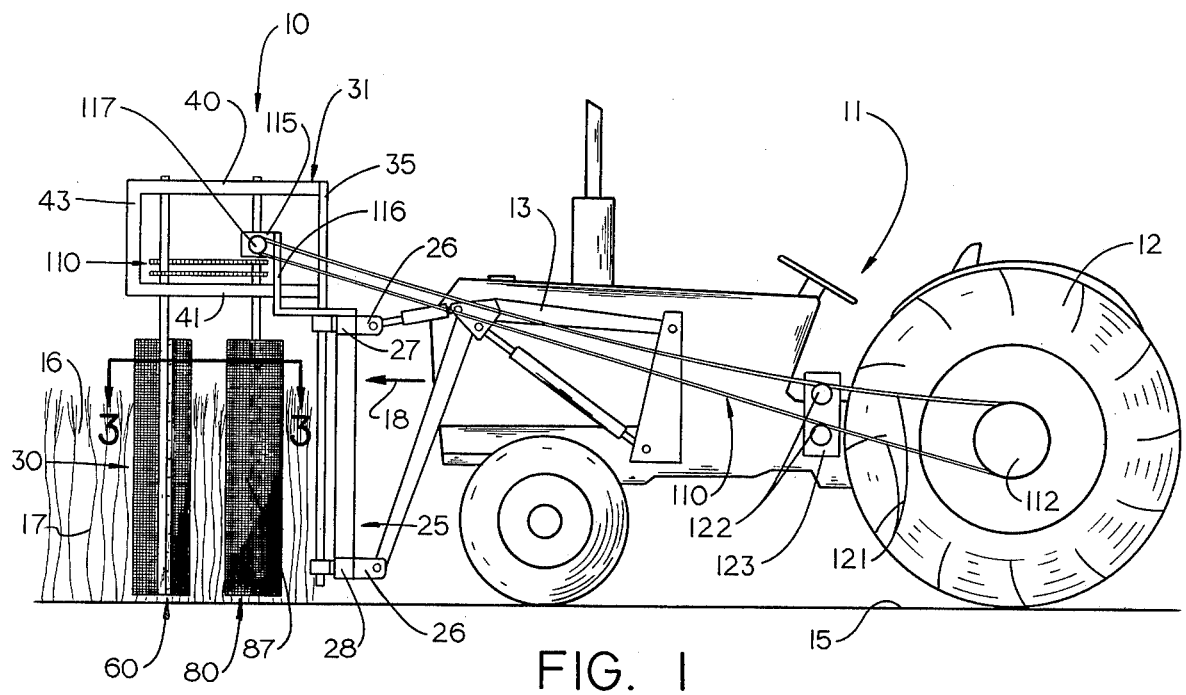
FIG. 1
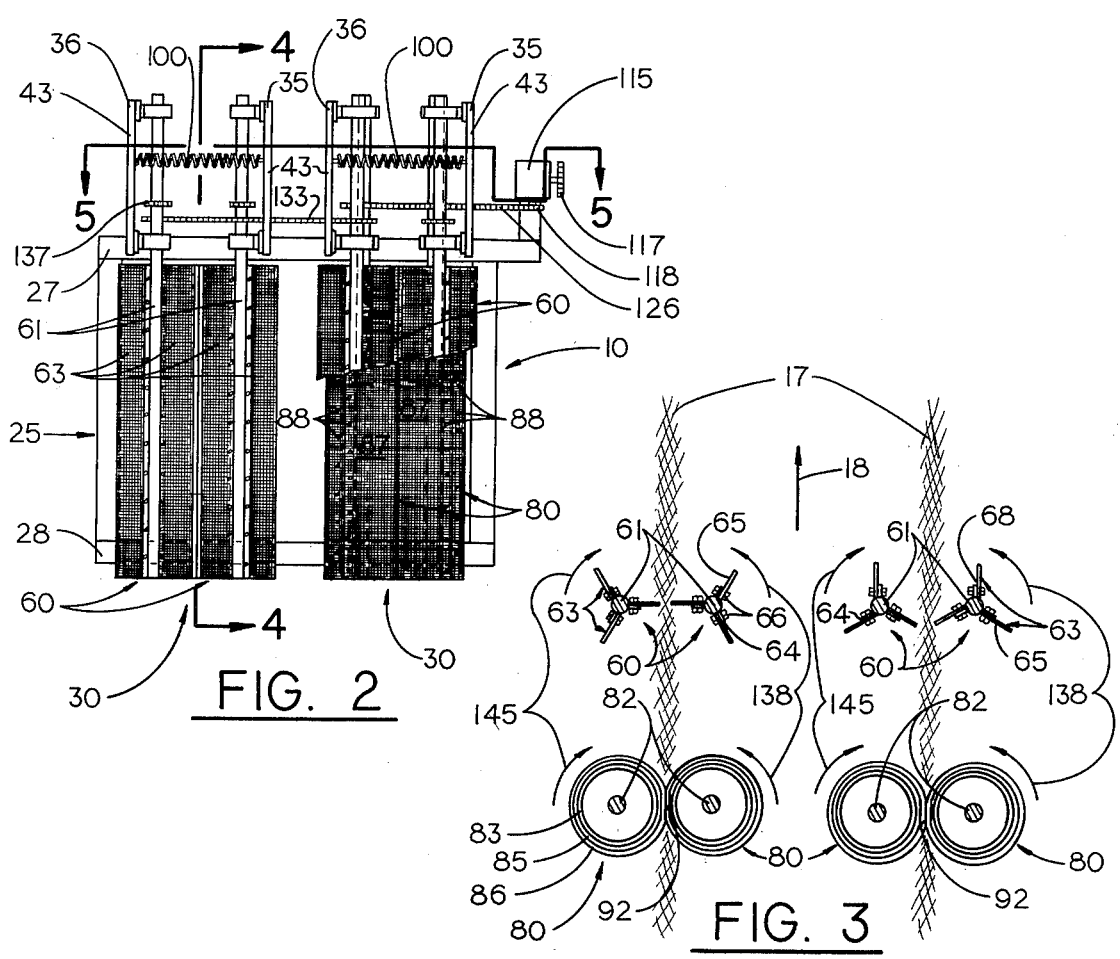
FIG. 2
FIG. 3

POLLINATING MACHINE

BACKGROUND OF THE INVENTION

1. Field of the Invention

The present invention relates to a pollinating machine and more particularly to such a machine for pollinating plants grown in a row, such as alfalfa grown for seed, by pressing the plants together transversely of the row.

2. Description of the Prior Art

In growing plants for seed production, it is desirable that a high proportion of the blossoms be pollinated in order to produce as much seed as possible for the investment in land, water, and labor. Alfalfa grown commercially is usually pollinated by bees, which only pollinate about ten percent of the alfalfa blossoms, although it is known that manual pressing of individual alfalfa blossoms at the proper time greatly increases the proportion of blossoms pollinated. Such manual pollination is not practical in alfalfa seed production and a variety of machines have been developed for pressing alfalfa plants to promote pollination. However, insofar as known to the applicant, none of these previous machines has been sufficiently successful to remain in use.

PRIOR ART STATEMENT

Characterizing the closest prior art of which the applicant is aware and in conformance with 37 C.F.R. §1.97 and §1.98, attention is invited to the following U.S. patents, copies of which are enclosed:

| Nielsen | 1,866,219 | July 5, 1932 |
| --- | --- | --- |
| Meiners | 2,171,160 | Aug. 29, 1939 |
| Kantack | 2,684,555 | July 27, 1954 |
| Hvistendahl | 2,685,149 | Aug. 3, 1954 |
| Chepil et al | 2,775,065 | Dec. 25, 1956 |
| Huey et al | 3,728,817 | Apr. 24, 1973 |

The Nielsen U.S. Pat. No. 1,866,219 is believed relevant in its disclosure of the pollination of alfalfa by pressing plants between pairs of driven pressing elements, and discloses several forms of machines for this purpose. One of the most pertinent forms has paired belts, as shown in FIGS. 7 and 8, and another pertinent form has paired cones, as shown in FIGS. 12 and 13. The belts and cones provide surfaces traveling oppositely to the direction of movement of a pollinating machine along a row. It is stated that the surfaces of the cones may be of "yieldable resilient material such as sponge rubber" and the belts have "yieldable means", evidently springs, as shown in FIG. 8, for urging the facing surfaces of the belts together. Unlike the present invention, the facing surfaces of the belts and the cones, as well as the corresponding surfaces of other forms of pollinating machines disclosed in the Nielsen patent, do not engage and are downwardly divergent. Another difference is that in all forms of the Nielsen machine the plants in each row are collected for pressing by plow-like elements 22, which precede these surfaces, and by positively rotated reels 24 which are "similar to those of binders and harvesters" and thus having rigid radially extended elements. Unlike the paddle wheels used for this purpose in the subject invention, the reels rotate about a horizontal axis and urge the plants downwardly since the pressing surfaces do not extend upwardly as far as the top of the plants.

The Meiners U.S. Pat. No. 2,171,160 is believed relevant in its disclosure of a machine providing a "squeezing action . . . to assist in the natural generation of the alfalfa seeds". This action is applied by the facing, parallel, and upright surfaces of a pair of endless belts 12 and 13 which are urged toward each other by rollers 18, 19, and 20 mounted on frames 16 and 17 urged together by springs 39. This patent states that the pressing portions of the belts "travel to the rear" at a rate of speed which is the "same as the ground speed". It appears from FIGS. 1, 2, and 3 that the pressing surfaces of the belts do not engage and the collecting of plants for pressing is performed, in contrast to the subject invention, by diverging portions of the belts disposed forwardly of the pressing area.

U.S. Pat. No. 2,684,555 to Kantack is believed relevant in its disclosure of generally upright power driven rollers having a "soft rubber covering". Unlike the subject invention, the rollers do not press the blossoms against other rollers but against flat "resilient pads" 14, and the plants are collected for pressing by plow-like elements.

The Hvistendahl U.S. Pat. No. 2,685,149 is believed relevant in its disclosure of upright, power driven rollers to press alfalfa plants for pollinating. Adjacent pairs of the rollers apparently do not engaged and are not movable toward each other, pollination being effected by a flow of heated air in a chamber following the rollers. Plants to be pollinated are guided between the rollers by elements which converge toward the spaces between the rollers.

The patent to Chepil et al. U.S. Pat. No. 2,775,065 discloses an "apparatus effecting the fecundation of plants" by collecting and distributing pollen. The apparatus is believed relevant in its inclusion of a powered rotary element, the brush 62, which unlike the rotary collecting elements of the subject invention, has a horizontal axis and follows the pollen releasing elements 38 which are swingable vanes.

U.S. Pat. No. 3,728,817 to Huey et al. discloses a device for preventing pollination by applying a binder to corn tassels. This patent is relevant in that it discloses, for use with a row of plants, a pair of axially erect rollers having a rubber periphery for pressing the plants. The rollers have their axes close enough so that the rollers are mutually compressed and so that one of the rollers may be driven by contact with the other roller.

SUMMARY OF THE INVENTION

It is an object of the present invention to provide an improved pollinating machine.

Another object is to provide such a machine for use with plants which are grown in a row and which can be pollinated by pressing blossoms of the plant transversely of the row.

Another object is to provide such a machine which, when used with alfalfa plants, pollinates a substantially higher proportion of the blossoms than are pollinated by bees.

Another object is to provide such a machine which rapidly pollinates a row of plants and which does not cause significant damage to the plants.

Another object is to provide such a machine which is easily mounted on existing agricultural implements and is convenient to use.

A further object is to provide improved elements and arrangements thereof in a pollinating machine which is of simple and economical construction, dependable, sturdy, and fully effective in carry out its intended purposes.

BRIEF DESCRIPTION OF THE DRAWINGS

FIG. 1 is a side elevation of a pollinating machine embodying the principles of the subject invention in a representative operating environment.

FIG. 2 is a front elevation of the machine of FIG. 1 at an enlarged scale with portions broken away for illustrative convenience.

FIG. 3 is a horizontal section at the scale of FIG. 2 taken on line 3—3 in FIG. 1.

DESCRIPTION OF THE PREFERRED EMBODIMENT

Figure 4:
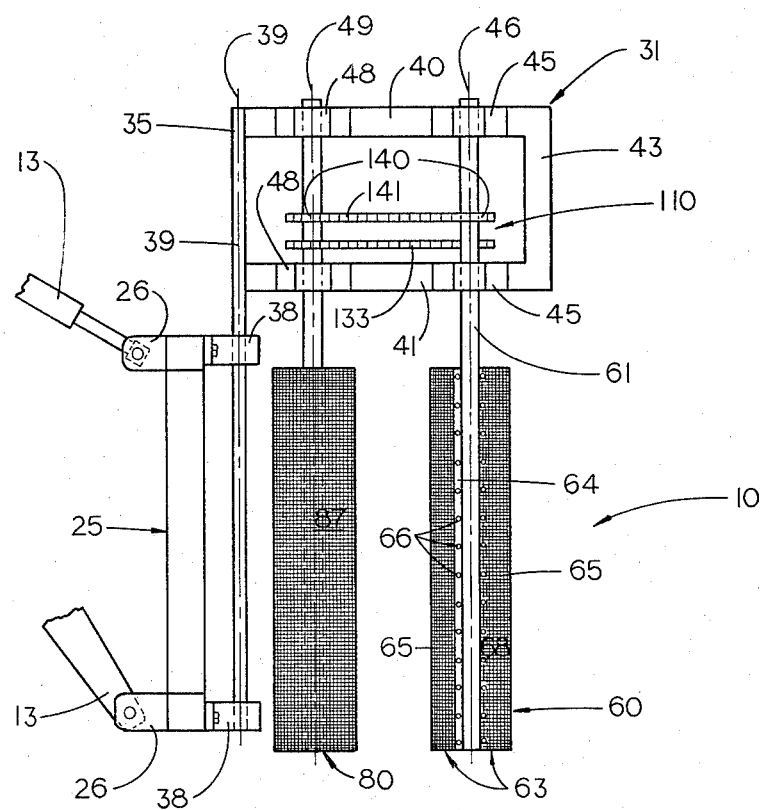
FIG. 4 is a vertical section of the machine, at the scale of FIG. 2 taken from the position of line 4—4 of FIG. 2.

Referring with greater particularlity to the drawings, in FIGS. 1 and 2 is shown a pollinating machine 10 embodying the principles of the present invention. The machine is, typically, mounted on and forwardly of any suitable tractor 11 which has a pair of rearward, ground engaging drive wheels 12, by a mounting 13. The mounting provides elevational positioning of the machine relative to the earth surface 15 while maintaining the machine in a predetermined attitude in relation to the horizontal and is of a well-known construction used for mounting a conventional front end loader or the like on the tractor. The machine is for use with blossoming plants 16, shown in FIGS. 1 and 3, which grow in parallel rows 17, the machine being transported along the rows by the tractor in a predetermined forward direction of movement indicated by the arrows 18 at a suitable ground traversing speed. The plants are of a kind, such as alfalfa plants grown for seed, whose pollination is facilitated by pressing the plants transversely of the row. The machine is depicted as being adapted to operate on two such rows, but as will be apparent, a similar machine could be constructed for operation on a single row or a greater plurality of rows.

The machine 10 has a main frame 25 which is fixed to the mounting 13 in any suitable manner, as by lugs 26, for elevational positioning thereby. The frame is of upright rectangular configuration and extends transversely across the rows 17. The frame has an upper bar 27 and a lower bar 28 which are horizontal and extend transversely across the rows, these bars being spaced vertically a distance substantially greater than the height of the plants.

The machine 10 has a pair of substantially identical pollinating units 30 mounted on the frame 25 and best shown in FIGS. 1, 2, and 4. Each unit is adapted for operation on one of the rows 17, the units being spaced transversely of the rows a distance substantially equal to the distance therebetween. Each unit has a movable frame 31 and a fixed frame 32. These frames are generally planar and extend in spaced relation in a direction generally parallel to the direction of movement 18. When the machine is in use, the frames of each unit are spaced transversely oppositely of a corresonding row. The movable frame has a column 35 which extends vertically upwardly from the bar 20 to a point substantially upwardly of the bar 27, and the fixed frame has a corresponding and coextensive column 36. The fixed and the movable frames are similar in construction except that the column of the fixed frame is of rectangular cross-section, and is rigidly connected to these bars, while the column of the movable frame is of circular cross-section and is received in a pair of bearing blocks 38 individual to the bars for pivotal movement about an upright pivotal axis 39.

Each of the frames 31 and 32 has an upper arm 40 and a lower arm 41 extended forwardly from the respective columns 35 or 36. The arms of each movable frame are pivotally movable about the corresponding axis 39. The arms of each frame are disposed in vertically spaced relation and are disposed upwardly of the upper bar 27 of the main frame 25. The arms of each frame are equal in length and are interconnected at their forward ends for rigidity by an upright 43. The arms mount individual bearing blocks 45 which are adjacent to the upright and define an upright paddle axis 46. The arms of each frame also mount individual bearing blocks 48 which are adjacent to the column and define an upright roller axis 49. It is evident that the paddle and the roller axes corresponding to the fixed frames are fixed in relation to the main frame.

The bearing blocks 45 and 48 of each unit 30 are disposed on the facing sides of the frames 31 and 32 of the unit. The blocks are disposed so that each corresponding pair of axes 46 and 49 are aligned in a direction normal to the direction 18 of movement while the pair of these axes corresponding to each frame are aligned in the direction of movement, the paddle axis being disposed in this direction from the roller axis. The roller axis of each movable frame is thus spaced along a corresponding row 17 in this direction from the pivotal axis 39 of this frame.

The frames 31 and 32 have individual and substantially identical paddle wheels 60, best shown in FIGS. 2, 3, and 4, which serve to collect or gather the plants as subsequently to be described. Each paddle wheel has an erect shaft 61 which is rotationally received in the corresponding pair of bearing blocks 45 so that the paddle wheel rotates about the axis 46 of this block with this axis substantially coincident with the shaft. Each shaft has a portion which extends axially downwardly from the corresponding lower arm 41 to a point somewhat downwardly of the bar 28, and this portion of the shaft has three paddles 63 extending along it in equally circumferentially spaced relation. Each paddle has a rigid plate 64, which is adjacent to the shaft and is fixed thereto in any suitable manner. A resiliently flexible rectangular element 65 is mounted on each plate in parallel engagement therewith. This element extends outwardly of the plate and radially from the shaft. For convenient replacement, the element is secured to the plate by a plurality of screws 66. The length of the elements radially of the shaft is such that the paths traced by the distal edges of the elements of each unit 30 are spaced somewhat apart centrally of a corresponding row 17. It has been found that a suitable material for the flexible element is a well-known and commercially available rubberized fabric material known as "rough top belting" having one side 68 which is of textured rubber material. This side is disposed in the direction of rotation of the paddle, this direction being determined in a manner subsequently to be described.

The frames 31 and 32 have individual and substantially identical pressing members or rollers 80. The roller are generally cylindrical and axially upright and extend downwardly from the corresponding lower arms 41 substantially the same distance as the paddle wheel shafts 61. Each roller has a shaft 82 extended axially through it and upwardly therefrom, the shaft being rotationally received in the corresponding bearing blocks 48. Each roller is thereby mounted on the arms 40 and 41 of the corresponding frame for rotation about the corresponding axis 49 with this axis substantially coincident with the center of the roller. As best shown in FIG. 3, each roller has a rigid cylindrical tube 83 mounted concentrically on the shaft in any suitable manner for rotation therewith. The roller has an inner peripheral layer 85 of relatively soft, rubber-like material wrapped about the tube and has an outer peripheral layer 86 of resiliently yielding, flexible material which is wrapped about the inner layer and provides a peripheral surface 87 of the roller. For convenient replacement the layers of each roller are secured to the corresponding tube by a plurality of screws 88. It has been found that the rough top belting material described above in connection with the elements 65 is well suited for use as the outer layer, the material being disposed with its textured side outward. It is evident that the peripheral surface is generally cylindrical and axially erect and is orbitally movable when the roller is rotated about its axis. It is evident that the pair of rollers of each unit 30 have peripheral portions disposed in facing relation and juxtapositioned centrally of a corresponding row 17. The exterior diameters of the rollers are such that, when the movable frame is substantially parallel to the fixed frame, these portions engage centrally of such a row in a somewhat flattened configuration as indicated by the numeral 92 in FIG. 3. It is also evident from the above description that the arms 40 and 41 of the movable frame 31 of each unit 30 are spaced transversely of the direction of movement 18 from the roller and the paddle wheel 60 of the corresponding fixed frame 32 and that these arms are mounted on the main frame 25 for pivotal movement about the corresponding axis 39 toward and from the roller and paddle wheel mounted on such fixed frame. The roller mounted on the movable frame is, therefore, mounted for movement transversely of a row 17 relative to the roller mounted on the fixed frame.

Figure 5:
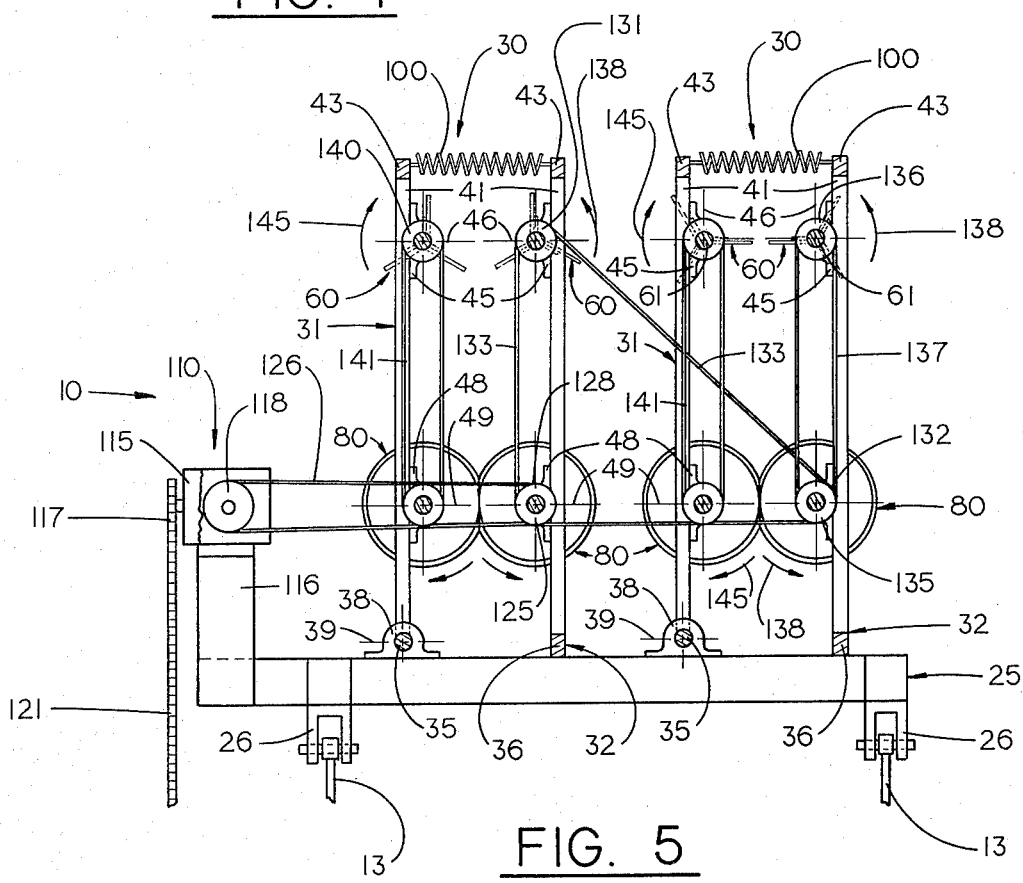
FIG. 5 is a horizontal section of the machine taken from the position of line 5—5 in FIG. 2 and at a further enlarged scale.

Each unit 30 has a helical tension spring 100, best shown in FIGS. 2 and 5, which interconnects its movable frame 31 and its fixed frame 32. The spring is horizontal and extends transversely between the uprights 43 of the interconnected frames at the ends of the arms 40 and 41 remote from the pivotal axis 39. The spring, therefore, resiliently urges the movable frame, together with its arms 40 and 41 to pivot toward the fixed frame and toward the roller 80 mounted thereon. The rollers and the paddle wheel 60 mounted on the movable frame are carried therewith, respectively, toward the rollers and the paddle wheel which are mounted on the fixed frame. The peripheral surfaces 87 of the rollers of each unit 30 are thus resiliently urged together so as to engage the portions 92 of the surfaces as the movable frame pivots toward the fixed frame.

The machine 10 has a rotational drive mechanism, best shown in FIGS. 1, 2, and 5 and indicated generally by the numeral 110, for rotationally driving the paddle wheels 60 and the rollers 80 about their respective axes 46 and 49. The mechanism includes a wheel sprocket 112 fixed in concentric relation to one of the drive wheels 12 of the tractor 11, the mechanism being thus powered by the tractor. The mechanism has a right-angle gear box 115 mounted on the main frame 25 by a bracket 116. The gear box is spaced transversely outwardly of the frames 31 and 32 at the side thereof corresponding to the wheel sprocket and is spaced upwardly of the rollers. The gear box has an input sprocket 117 which is aligned with the wheel sprocket and rotates about an axis substantially parallel to the axis thereof. The gear box has an output sprocket 118, which is spaced upwardly of the lower arms 41. The output sprocket is rotationally driven from the input sprocket about an axis substantially parallel to the axes of the rollers. The driving sprocket and the wheel sprocket are linked by an endless chain 121. This chain has upper and lower runs which are individually supported by a pair of idler sprockets 122 mounted on the tractor 11 in any suitable disposition by a bracket 123.

The pollinating unit 30 disposed toward the gear box 115 has a driven sprocket 125. This driven sprocket is fixed to the shaft 82 of the roller 80 mounted on the fixed frame 32 of this unit. This driven sprocket is aligned axially with the driving sprocket 118 of the gear box and is linked therewith by an endless chain 126 so that such roller shaft is rotationally driven from the sprocket 112 mounted on the tractor wheel 12. This roller shaft has a driving sprocket 128 mounted below and adjacent to its driven sprocket. The paddle wheel shaft 61 mounted on the fixed frame of this pollinating unit and the roller shaft mounted on the fixed frame of the other pollinating unit have respective driven sprockets 131 and 132 disposed at the same elevation as the sprocket 128. An endless chain 133, which is of triangular configuration as shown in FIG. 5, is looped outwardly about these three sprockets. The last mentioned roller shaft is provided with a sprocket 135 upward of its driven sprocket 132, and the paddle wheel shaft mounted on the same fixed frame has a driven sprocket 136 aligned with this driven sprocket and linked therewith by an endless chain 137. The sprockets 118, 125, 128, 131, 132, 135, and 136 are substantially identical so that all of the shafts mounting these sprockets, together with the paddle wheels and rollers mounted on the fixed frames, are driven at the same rotational speed and in the same direction as is indicated by the arrows 138 in FIGS. 2, 3, and 5. This direction is counter-clockwise as viewed in FIGS. 3 and 5 wherein the machine 10 and the tractor 11 are depicted as moving along the row in the direction 18. This rotational direction is established in any suitable manner as by the configuration and disposition of the gear box 115. The relative sizes of the wheel sprocket 12 and the input sprocket 117 of the gear box are such that the peripheral speed of the rollers mounted on the fixed frames 32 is substantially equal to the ground traversing speed of the machine and tractor. However, due to this direction of rotation, the engaging portions 92 of these rollers move in a direction opposite to the direction 18 as do the paddles 63 of the paddle wheels 60 mounted on the fixed frames when these paddles extend toward the center of a row 17.

The rotational drive mechanism 110 further includes, for each pollinating unit 30, a pair of elevationally aligned, substantially identical sprockets 140 individual to each shaft 82 and to each shaft 61 mounted on the movable frame 31 of the unit, each such pair being linked by an endless chain 141. Since the rollers 80 of each pollinating unit engage at their portions 92 with the roller mounted on the fixed frame 32 being rotationally driven as previously described, the roller on the movable frame is rotationally driven by the roller on the fixed frame at substantially the same rotational speed, but in the opposite direction. The paddle wheels mounted on the movable frames are driven from, and in the same direction as, the rollers mounted thereon by the sprockets 140 and chains 141, this common direction of rotation being indicated by the arrows 145.

It is evident that, as best shown in FIG. 3, the rollers 80 and the paddle wheels 60 mounted on the fixed frames 32 are driven by the mechanism 110 counter-rotationally to the paddle wheels and rollers mounted on the movable frames 31 with the peripheral speed of the rollers being substantially equal to the ground traversing speed of the machine 10 and tractor 11. It is also evident that the peripheral surfaces 87 of the rollers orbit the corresponding axes 45 with the engaging portions 92 of the surfaces moving oppositely of the direction 18, and it is apparent that, as the machine moves along the rows 17, the rotational drive mechanism drives the paddle wheels so that, as the paddle wheels approach the plants 16, the paddles move toward the centers of their corresponding rows.

OPERATION

The operation of the described embodiment of the present invention is believed to be clearly apparent and is briefly summarized at this point. When the machine 10 is in use, as shown in FIGS. 1 and 3, it is transported along the rows 17 by the tractor 11 with the machine elevationally positioned by the mounting 13 so that the paddle wheels 60 and the rollers 80 are generally aligned elevationally with the plants 16. The tractor is guided in a well-known manner so that the centers of two of the rows are individually aligned in the direction of motion 18 centrally between axes 46 and 49 of the pollinating units 30. As the machine moves along the two rows the rollers and paddle wheels of each unit are, therefore, disposed transversely oppositely of a corresponding one of the rows.

As the machine 10 moves in the direction 18 the paddles 63 of each unit 30 engage the plants 16 of the corresponding rows 17 as the paddles approach the plants so that the paddles urge the plants centrally of the row and centrally between the paddle wheels 60 with the result that the plants are subsequently engaged between the rollers 80 of the unit and pressed together between the engaging portions 92 of their peripheral surfaces 87. Thus it is evident that the paddle wheels are disposed in the direction of movement from the rollers and serve to gather the plants for subsequent pressing between such peripheral surfaces.

As each of the plants 16 passes between the engaging pairs of rollers 80, the blossoms of the plant are pressed transversely of the corresponding row 17 by the outer peripheral layers 86 thereby facilitating pollination of the blossoms. Since this layer is relatively flexible and is backed by the soft inner layer 85, the blossoms and the plants are not injured by such pressing. Further to avoid injury to the plants and to maintain the rollers in pressing engagement therewith, the one of the rollers mounted on the movable frame 31 moves from the corresponding roller on the fixed frame 32 against the urging of the corresponding spring 100 when relatively large plants and/or clumps of plants are engaged between the rollers. Subsequently, the spring urges the movable frame to pivot back toward the fixed frame so as to maintain the rollers in pressing engagement with the plants to insure pollination of their blossoms. Since the engaging portions 92 of the peripheral surfaces 87 of the rollers move at a speed which is opposite in direction and substantially equal to the ground traversing speed of the machine 10 and the rollers, there is substantially no relative velocity in a direction along the row between the plants and the engaging portions of the rollers. As a result, the rollers press the plants transversely of the rows, but do not tend to displace them relative to the earth surface 15 in a direction along the rows, further avoiding significant injury to the plants as they are pollinated by the machine 10.

Although the invention has been herein shown and described in what is conceived to be the most practical and preferred embodiment, it is recognized that departures may be made therefrom within the scope of the invention, which is not to be limited to the illustrative details disclosed.

Having described my invention, what I claim as new and desire to secure by Letters Patent is:

1. A machine for operating on plants growing in a row, the machine comprising a pair of generally cylindrical pressing members, means mounting the members for movement along the row in a predetermined direction and for rotation about individual erect axes spaced transversely of the row, the members having individual facing peripheral portions which are juxtapositioned centrally of the row and one of the pressing members being mounted for movement relative to the other pressing member in a direction transversely of the row; means for rotationally driving the members with such portions moving in a direction opposite said direction, and means for resiliently urging the one member toward the other member to engage such portion of the one member with such portion of the other member so that the plants are engaged between such portions and pressed together thereby transversely of the row as the machine moves therealong.

2. The machine of claim 1 further comprising a pair of collecting members mounted by the mounting means for rotation about individual, erect axes spaced transversely of the row, each collecting member being spaced in said direction from the transversely corresponding one of the pressing members; and means for driving each collecting member in the same rotational direction as the transversely corresponding pressing member, each collecting member having a plurality of radially extended flexible elements disposed to engage the plants and urge the plants centrally of the row for subsequent pressing between the pressing members.

3. A pollinating machine for use with an implement moving at a ground traversing speed in a predetermined direction along a row of plants to be pollinated by pressing the plants transversely of the row, the machine comprising:
 A. a pair of members bearing individual, orbitally movable upright surfaces having individual portions which engage centrally of the row;
 B. powered means for orbiting the surfaces at a relative speed substantially equal to the ground traversing speed with the engaging portions moving oppositely of the predetermined direction;
 C. means mounted in spaced relation in the direction of movement from the surfaces for gathering the plants centrally of the row for subsequent pressing between the surfaces;
 D. means mounting the surfaces, the resilient means, and the gathering means on such an implement for movement therewith along the row, said means including an arm orbitally mounting one of the members and movable about an upright pivotal axis spaced along the row from said portions; and E. means resiliently urging the arm to pivot toward the other of the members.

4. The machine of claim 3 wherein said members are axially upright, generally cylindrical rollers having individual axes spaced transversely of the row, and the surfaces are the respective peripheral surfaces of the rollers; wherein the mounting means mounts each roller for rotation about the axis thereof; and wherein the powered means drives the rollers counter-rotationally at a rotational speed such that the peripheral speed of each roller is substantially equal to ground traversing speed.

5. The machine of claim 4 wherein the periphery of each roller is a layer of resiliently yielding material.

6. A pollinating machine for use with an implement moving at a ground traversing speed in a predetermined direction along a row of plants to be pollinated by compressing the plants transversely of the row, the machine comprising:

A. a pair of members bearing individual, orbitally movable upright surfaces having individual portions disposed centrally of the row;

B. means disposed in the direction of movement from the surfaces for gathering the plants centrally of the row for subsequent pressing between the surfaces, such means having a pair of upright shafts rotatable about individual axes spaced transversely of the row and having a plurality of resiliently flexible plant engaging elements extended generally radially outwardly from each shaft;

C. powered means for orbiting the surfaces at a speed substantially equal to the ground traversing speed with the engaging portions moving oppositely of the predetermined direction and for driving the shafts counter-rotationally with said elements moving toward the center of the row as the elements approach the plants; and D. means mounting the surfaces and the gathering means on such an implement for movement therewith along the row.

7. The machine of claim 6 wherein the mounting means mounts one of the members for movement toward and from the other of the members, and the machine further comprises means resiliently urging the one member toward the other member.

8. A pollinating machine for use with plants growing along a row and having blossoms which are pollinated when the plants are compressed transversely of the row, the machine being for use with an implement traversing the earth surface in a predetermined direction along the row and comprising:

A. a frame adapted to mount on the implement for movement therewith;

B. a pair of rollers each having a generally cylindrical, axially erect periphery of resiliently yielding material;

C. a pair of collectors each having an erect shaft and a plurality of resiliently flexible elements extending along the shaft and radially therefrom in spaced relation thereabout;

D. means mounting one roller and one collector for rotation about individual axes which are, respectively, substantially coincident with the center of the said one roller and with the shaft of said one collector, said axes being mounted in fixed relation to the frame and generally aligned in said predetermined direction with the one collector disposed in said direction from the one roller;

E. an arm mounted on the frame for pivotal movement about an erect axis and extended therefrom in a direction generally parallel to said predetermined direction, the arm being spaced from the one roller and the one collector in a direction normal to said direction and pivotable about said axis toward and from the one roller and the one collector;

F. means mounting the other roller and the other collector on the arm for rotation about individual axes which are, respectively, substantially coincident with the center of said other roller and with the shaft of said other collector and which are generally aligned in said predetermined direction, the axis of said other collector being aligned with the axis of said one collector in a direction normal to said direction and the axes of the rollers being spaced transversely of said direction and disposed therealong so that the peripheries of the rollers engage as the arm pivots toward said one roller and said one collector;

G. means for resiliently urging the arm to pivot in a direction toward said one roller and said one collector so as to carry said other roller into peripheral engagement with said one roller; and H. means for rotationally driving the rollers and the collectors about their respective axes with the peripheral speed of each roller substantially equal to the ground traversing speed in said predetermined direction and with the peripheries of the rollers and the radially extending elements of the collectors moving centrally of the row in a direction opposite to said direction so that, as the machine moves along the row with the collectors and the rollers disposed transversely oppositely thereof, said elements of the collectors collect the plants centrally thereof for subsequent compressing engagement between the peripheries of the rollers.

* * * * *

UNITED STATES PATENT AND TRADEMARK OFFICE
CERTIFICATE OF CORRECTION

PATENT NO. : 4,383,389

DATED : May 17, 1983

INVENTOR(S) : Paul A. Bezzerides

It is certified that error appears in the above-identified patent and that said Letters Patent is hereby corrected as shown below:

Column 2, line 25, delete "engaged" and substitute ---engage---.

Column 3, line 65, delete "20" and substitute ---28---.

Signed and Sealed this

Nineteenth Day of July 1983

[SEAL]

Attest:

GERALD J. MOSSINGHOFF

Attesting Officer

Commissioner of Patents and Trademarks